(12) United States Patent
Chari et al.

(10) Patent No.: US 6,333,410 B1
(45) Date of Patent: Dec. 25, 2001

(54) PROCESS FOR THE PREPARATION AND PURIFICATION OF THIOL-CONTAINING MAYTANSINOIDS

R
1 a: CH₃,
  b: CH₂CH₃,
  c: CH(CH₃)₂,
  d: (CH₂)₂CH₃, or
  e: CH₂CH(CH₃)₂ reducing agent

| | X |
|---|---|
| 3 a: | CH$_2$ |
| b: | (CH$_2$)$_2$ |
| c: | (CH$_2$)$_3$ |
| d: | (CH$_2$)$_4$ |
| e: | CH(CH$_3$)CH$_2$ |

| | X |
|---|---|
| 4 a: | CH$_2$ |
| b: | (CH$_2$)$_2$ |
| c: | (CH$_2$)$_3$ |
| d: | (CH$_2$)$_4$ |
| e: | CH(CH$_3$)CH$_2$ |

Fig. 2b 3 b

| 5 a: | x = H |
|---|---|
| b: | x = NO$_2$ |

Fig. 2c

| | X | R |
|---|---|---|
| 6 a: | CH$_2$ | CH$_3$ |
| b: | (CH$_2$)$_2$ | CH$_3$ |
| c: | (CH$_2$)$_3$ | CH$_3$ |
| d: | (CH$_2$)$_4$ | CH$_3$ |
| e: | (CH$_2$)$_2$ | C$_6$H$_5$ |
| f: | (CH$_2$)$_2$ | p-NO$_2$C$_6$H$_4$ |
| g: | CH(CH$_3$)CH$_2$ | CH$_3$ |

Fig. 3a

R = CH₃, higher alkyl, aryl

| | n | |
|---|---|---|
| 7 a: | 1: *N*-methyl-*L*-cysteine | 8 a: 1 |
| b: | 2: *N*-methyl-*L*-homocysteine | b: 2 |

Fig. 3b n
9 a: 1
b: 2 x = 0 - 10
R = CH₃, higher alkyl, aryl

PROCESS FOR THE PREPARATION AND PURIFICATION OF THIOL-CONTAINING MAYTANSINOIDS

FIELD OF THE INVENTION

The present invention relates to a process for preparing and purifying cytotoxic agents. More specifically, the invention relates to a process for preparing and purifying cytotoxic agents comprising thiol-containing maytansinoids. These cytotoxic agents can be used as therapeutic agents by linking them to a cell binding agent, through the thiol group, and then delivering them to a specific cell population in a targeted fashion.

BACKGROUND OF THE INVENTION

In recent years, a myriad of reports have appeared on the attempted specific targeting of tumor cells with monoclonal antibody-drug conjugates (R. V. J. Chari., 31 *Adv. Drug Deliv. Res.*, 89–104 (1998); G. A. Pietersz and K. Krauer, 2 *J. Drug Targeting* 183–215 (1994); Sela et al., in *Immunoconjugates* 189–216 (C. Vogel, ed. 1987); Ghose et al., in *Targeted Drugs* 1–22 (E. Goldberg, ed. 1983); Diener et al., in *Antibody mediated delivery systems* 1–23 (J. Rodwell, ed. 1988); Pietersz et al., in *Antibody mediated delivery systems* 25–53 (J. Rodwell, ed. 1988); Bumol et al., in *Antibody mediated delivery system* 55–79 (J. Rodwell, ed. 1988). Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al., 46 *Cancer Res.* 2407–2412 (1986); Ohkawa et al., 23 *Cancer Immumol. Immunother.* 81–86 (1986); Endo et al., 47 *Cancer Res.* 1076–1080 (1980)), dextran (Hurwitz et al., 2 *Appl. Biochem.* 25–35 (1980); Manabi et al., 34 *Biochem. Pharmacol.* 289–291 (1985); Dillman et al., 46 *Cancer Res.* 4886–4891 (1986); Shoval et al., 85 *Proc. Natl. Acad. Sci.* 8276–8280 (1988)), or polyglutamic acid (Tsukada et al., 73 *J. Natl. Canc. Inst.* 721–729 (1984); Kato et al., 27 J. Med. Chem. 1602–1607 (1984); Tsukada et al., 52 *Br. J. Cancer* 111–116 (1985)).

A wide array of linker technologies have been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (102 *Biochem. Biophys. Res. Commun.* 1048–1054 (1981)). Yang and Reisfeld used the same technique to conjugate daunorubicin to an anti-melanoma antibody (80 *J. Natl. Canc. Inst.* 1154–1159 (1988)). Dillman et al. also used an acid-labile linker in a similar fashion to prepare conjugates of daunorubicin with an anti-T cell antibody (48 *Cancer Res.* 6097–6102 (1988)). Trail et al. linked doxorubicin to antibodies via an acid-labile hydrazone bond (52 *Cancer Res.* 5693–5700 (1992)).

An alternative approach, explored by Trouet et al., involved linking daunorubicin to an antibody via a peptide spacer arm (79 *Proc. Natl. Acad. Sci.* 626–629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al., 260 *J. Biol. Chem.* 12035–12041 (1985); Lambert et al., in *Immunotoxins* 175–209 (A. Frankel, ed. 1988); Ghetie et al., 48 *Cancer Res.* 2610–2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al. described the conversion of methotrexate into a mercaptoethylamide derivative followed by conjugation with poly-D-lysine via a disulfide bond (260 *J. Biol. Chem.* 10905–10908 (1985)). A recent report described the preparation of a conjugate of the trisulfide-containing toxic drug calicheamicin with an antibody (L. M. Hinman et al., 53 *Cancer Res.* 3336–3342 (1993); E. L. Sievers et al., 93 *Blood* 3678–3684 (1999).

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin and vincristine. For example, an antibody conjugate of doxorubicin was evaluated in human clinical trials, and found to be ineffective (Tolcher et al., 17 *J. Clinical Oncol.* 478–484 (1999)). In order to achieve significant cytotoxicity, linkage of a large number of drug molecules either directly to the antibody or through a polymeric carrier molecule becomes necessary. However, such heavily modified antibodies often display impaired binding to the target antigen and fast in vivo clearance from the blood stream.

Maytansinoids are highly cytotoxic drugs. Maytansine was first isolated by Kupchan et al. from the east African shrub *Maytenus serrata* and shown to be 100 to 1000 fold more cytotoxic than conventional cancer chemotherapeutic agents like methotrexate, daunorubicin, and vincristine (U.S. Pat. No. 3,896,111). Subsequently it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al., 21 *J. Med. Chem.* 31–37 (1978); Higashide et al., 270 *Nature* 721–722 (1977); Kawai et al., 32 *Chem. Pharm. Bull.* 3441–3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters can be classified into two groups:

(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and (b) C-3 esters with derivatives of N-methyl-L-alanine (U.S. Pat. Nos. 4,137,230; 4,260,608; 5,208,020; 5,416,064; and 12 Chem. Pharm. Bull. 3441 (1984)).

Esters of group (b) were found to be much more cytotoxic than esters of group (a).

Maytansine is a mitotic inhibitor. Treatment of L1210 cells in vivo with maytansine has been reported to result in 67% of the cells accumulating in mitosis. Untreated control cells were reported to demonstrate a mitotic index ranging from between 3.2 to 5.8% (Sieber et al., 43 *Comparative Leukemia Research* 1975, *Bibl. Haemat.* 495–500 (1976)). Experiments with sea urchin eggs and clam eggs have suggested that maytansine inhibits mitosis by interfering with the formation of microtubules through the inhibition of the polymerization of the microtubule protein, tubulin (Remillard et al., 189 *Science* 1002–1005 (1975)).

In vitro P388, L1210, and LY5178 murine leukemic cell suspensions have been found to be inhibited by maytansine at doses of $10^{-3}$ to $10^{-1}$ microgram/mL, with the P388 line being the most sensitive. Maytansine has also been shown to be an active inhibitor of in vitro growth of human nasopharyngeal carcinoma cells. The human acute lymphoblastic leukemia line C.E.M. was reported inhibited by concentrations as low as $10^{-7}$ microgram/ml (Wolpert-DeFillippes et al., 24 *Biochem. Pharmacol.* 1735–1738 (1975)).

In vivo, maytansine has also been shown to be active. Tumor growth in the P388 lymphocytic leukemia system was shown to be inhibited over a 50- to 100-fold dosage range which suggested a high therapeutic index; also significant inhibitory activity could be demonstrated with the L1210 mouse leukemia system, the human Lewis lung carcinoma system and the human B-16 melanocarcinoma system (Kupchan, 33 *Ped. Proc.* 2288–2295 (1974)).

Because the maytansinoids are highly cytotoxic, they were expected to be of use in the treatment of many diseases such as cancer. This expectation has yet to be realized. Clinical trials with maytansine were not favorable due to a number of side effects (Issel et al., 5 *Can. Trtmnt. Rev.* 199–207 (1978)). Adverse effects to the central nervous system and gastrointestinal symptoms were responsible for some patients refusing further therapy (Issel at 204), and it appeared that maytansine was associated with peripheral neuropathy that might be cumulative (Issel at 207).

However, forms of maytansinoids that are highly cytotoxic, yet can still effectively be used in the treatment of many disease, have been described (U.S. Pat. Nos. 5,208,020 and 5,416,064; Chari et al., 52 *Cancer Res.* 127–131 (1992); Liu et al., 93 *Proc. Natl. Acad. Sci.* 8618–8623 (1996)).

A further drawback to the therapeutic use of maytansinoids, of interest here, is that the process for the preparation and purification of thiol-containing maytansinoids involves several inefficient chromatographic steps that are cumbersome, not easily scalable and result in only moderate yields.

U.S. Pat. Nos. 5,208,020 and 5,416,064 disclose that a thiol-containing maytansinoid may be produced by first converting a maytansinoid bearing an ester group into maytansinol, then esterifying the resulting maytansinol with N-methyl-L-alanine or N-methyl-L-cysteine derivatives to yield disulfide-containing maytansinoids, followed by cleavage of the disulfide group with dithiothreitol to the thiol-containing maytansinoids. However, this process involves several inefficient steps that are cumbersome and result in moderate yields.

More specifically, maytansinol is first derived from maytansine or other esters of maytansinol by reduction, such as with lithium aluminum hydride. (Kupchan, S. M. et al., 21 *J. Med. Chem.* 31–37 (1978); U.S. Pat. No. 4,360,462). It is also possible to isolate maytansinol from the microorganism *Nocardia* (see Higashide et al., U.S. Pat. No. 4,151,042). In a specific example, the conversion of Ansamitocin P-3 into maytansinol by reductive hydrolysis with lithium aluminum hydride in tetrahydrofuran at −5° C. was described in U.S. Pat. No. 4,162,940. However, the reaction with lithium aluminum hydride results in the formation of several side products which can be removed only by careful preparative thin layer chromatography on silica gel. Thus, this process is not amenable for industrial scale use.

The next step in the process is the conversion of maytansinol to different ester derivatives using N-methyl-L-alanine or N-methyl-L-cysteine derivatives, and suitable agents such as dicyclohexylcarbodiimide (DCC) and catalytic amounts of zinc chloride (see U.S. Pat. No. 4,137,230; Kawai et al., 32 *Chem. Pharm. Bull.* 3441–3951 (1984); U.S. Pat. No. 4,260,609). Two diastereomeric products containing the D and L-aminoacyl side chains result, as does a small portion of unreacted maytansinol. While the unreacted maytansinol is readily separated from its esters by column chromatography on silica gel, the diastereomeric maytansinoid esters are barely separable. In the process previously described (Kupchan, S. M., 21 *J. Med. Chem.* 31–37 (1978); U.S. Pat. No. 4,360,462), the desired L-aminoacyl ester is obtained after purification over two silica gel columns followed by further purification by preparative thin layer chromatography on silica gel. Thus, this process is also not amenable for industrial scale use.

The last step in the process, the reduction of the disulfide-containing maytansinoids to the corresponding thiol-containing maytansinoids, is achieved by treatment with dithiotlireitol (DTT), purification by HPLC using a C-18 column and elution with a linear gradient of 55% to 80% acetonitrile in $H_2O$. However, this step results in low yields and is also not amenable for industrial scale use. Thiol-containing maytansinoids are not very soluble in the ethanol/water solvent mixture used for the reaction. Furthermore, purification by HPLC on a reverse phase C-18 column using acetonitrile/water as the mobile phase results in poor recovery and can result in the dimerization of some product.

Accordingly, an improved process for the preparation and purification of thiol-containing maytansinoids, that reduces the complexity of the process, allows scalability and increases the yield, is greatly needed.

SUMMARY OF THE INVENTION

Thus, the object of the present invention is to provide an improved process for the preparation and purification of thiol-containing maytansinoids that reduces the complexity of the process, allows scalability and improves the yield.

This and other objectives have been achieved by providing an improved process for the preparation and purification of thiol-containing maytansinoids.

In one embodiment, the present invention provides a process for preparing a thiol-containing maytansinoid comprising the steps of:

(1) conducting reductive hydrolysis of a maytansinoid C-3 ester with a reducing agent selected from the group consisting of lithium trimethoxyaluminum hydride (LiAl(OMe)₃H), lithium triethoxyaluminum hydride (LiAl(OEt)₃H), lithium tripropoxyaluminum hydride (LiAl(OPr)₃H), sodium trimethoxyaluminum hydride (NaAl(OMe)₃H), sodium triethoxyaluminum hydride (NaAl(OEt)₃H) and sodium tripropoxyaluminum hydride (NaAl(OPr)₃H), to yield a maytansinol;

(2) purifying the maytansinol to remove side products when present;

(3) esterifying the purified maytansinol with a carboxylic acid to yield a reaction mixture of an L- and a D-aminoacyl ester of maytansinol;

(4) separating the L-aminoacyl ester of maytansinol from the reaction mixture in (3);

(5) reducing the L-aminoacyl ester of maytansinol to yield a thiol-containing maytansinoid; and (6) purifying the thiol-containing maytansinoid.

Preferably, the reducing agent in (1) is lithium trimethoxyaluminum hydride.

Also preferably, the reducing agent in (1) is used in a concentration of from about 5 to 100 equivalents per mole of the maytansinoid C-3 ester. More preferably, the reducing agent in (1) is used in a concentration of from about 7.5 to 30 equivalents per mole of the maytansinoid C-3 ester. Most preferably, the reducing agent in (1) is used in a concentration from about 10 to 20 equivalents per mole of the maytansinoid C-3 ester.

Preferably, the reductive hydrolysis in (1) is conducted at a temperature of from about −80° C. to 0° C. More preferably, the reductive hydrolysis in (1) is conducted at a temperature of from about −45° C. to −27.5° C. Most preferably, the reductive hydrolysis in (1) is conducted at a temperature of from about −35° C. to −30° C.

Preferably, the reducing agent in (1) is added over a period of from about 5 to 40 minutes. More preferably, the reducing agent in (1) is added over a period of from about 7 to 20 minutes. Most preferably, the reducing agent in (1) is added over a period of from about 8 to 12 minutes.

Preferably, the maytansinol is purified in (2) by chromatography. More preferably, the maytansinol is purified in (2) by chromatography where the chromatography is silica gel column chromatography, preparative thin-layer chromatography on silica gel or cyano-bonded silica HPLC column chromatography. Most preferably, the maytansinol is purified in (2) by chromatography where the chromatography is silica gel column chromatography.

Preferably, the purification in (2) is performed at ambient temperature.

Preferably, the maytansinol in (2) is purified to a purity of about 95%.

Preferably, the carboxylic acid in (3) is selected from the group consisting of N-methyl-N-methyldithioacetyl-L-alanine, N-methyl-N-(3-methyldithio-propanoyl)-L-alanine, N-methyl-N-(3-methyldithio-butanoyl)-L-alanine, N-methyl-N-(4-methyldithio-butanoyl)-L-alanine, N-methyl-N-(5-methyldithio-pentanoyl)-L-alanine, N-methyl-N-(3-phenyldithio-propanoyl)-L-alanine, N-methyl-N-[3-(4-nitrophenyldithio)-propanoyl]L-alanine, N-acetyl-N-methyl-methyldithiocysteine and N-acetyl-N-methylmethyldithiohomocysteine. More preferably, the carboxylic acid in (3) is N-methyl-N-(3-methyldithio-propanoyl)-L-alanine.

Preferably, the esterification in (3) is conducted at ambient temperature.

Preferably, the esterification in (3) further comprises the use of dicyclohexylcarbodiimide and zinc chloride.

Preferably, the separating in (4) is carried out by passing the reaction mixture over a cyano-bonded silica HPLC column.

Preferably, the separating in (4) is carried out at about 25° C.

Preferably, the reduction in (5) uses dithiothreitol as the reducing agent.

Preferably, the reduction in (5) is carried out in a mixture of ethyl acetate-methanol-aqueous buffer which is capable of keeping buffer salts, dithiothreitol, unreduced maytansinoids and reduced maytansinoids in solution. More preferably, the mixture of ethyl acetate-methanol-aqueous buffer is 1:1.5:1, v/v/v, ethyl acetate:methanol:aqueous buffer.

Preferably, the concentration of the thiol-containing maytansinoid is such that the thiol-containing maytansinoid remains soluble in ethyl acetate-methanol-aqueous buffer. Preferably, the concentration of the thiol-containing maytansinoid is about 4 g/L.

Preferably, the reduction in (5) is carried out in an oxygen-free atmosphere.

Preferably, the reduction in (5) is carried out at about 25° C.

Preferably, the purification of the thiol-containing maytansinoid in (6) is by chromatography. More preferably, the chromatography is by a cyano-bonded HPLC column. Most preferably, the chromatography is by a cyano-bonded HPLC column equilibrated and run in an organic solvent. Preferably, the organic solvent is a mixture of hexanes:2-propanol:ethyl acetate, more preferably the solvent is a 78.0:5.5:16.5, v/v/v, mixture of hexanes:2-propanol:ethyl acetate.

DETAILED DESCRIPTION OF THE INVENTION

This invention is based on the synthesis of thiol-containing maytansinoid derivatives that retain high cytotoxicity and that can be effectively linked to cell binding agents. The art reveals that the existing methods for producing thiol-containing maytansinoids are complex, non-scalable and produce low product yield. The present invention overcomes these problems by disclosing a novel process for producing thiol-containing maytansinoids that reduces the complexity of the process, allows scalability and improves product yield.

Thus, the invention provides a novel process for the production of thiol-containing maytansinoids, useful agents for the elimination of diseased or abnormal cells that are to be killed or lysed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

These thiol-containing maytansinoids can be chemically linked to a cell binding agent while keeping a high cytotoxicity either in bound form or in released form or in both states. High cytotoxicity is defined as exhibiting a toxicity having an $IC_{50}$—the inhibiting concentration of a toxic substance that leaves a surviving fraction of 0.5—of about $10^{-8}$ M or less when measured in vitro with KB cells upon a 24 hour exposure time to the drug.

The effectiveness of the compounds of the invention as therapeutic agents depends on the careful selection of an appropriate cell binding agent. Cell binding agents may be of any kind presently known, or that become known and include peptides and non-peptides. Generally, these can be antibodies (especially monoclonal antibodies), lymphokines, hormones, growth factors, nutrient-transport molecules (such as transferrin), or any other cell binding molecule or substance.

Suitable Maytansinoids

There have been a number of disclosures that teach the production of maytansinoids and maytansinoid derivatives that may be used as a cytotoxic agent. Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring, and the process for their production, include:

(1) C-19-dechloro (U.S. Pat. No. 4,256,746) (prepared by lithium aluminum hydride reduction of ansamitocin P-2);

(2) C-20-hydroxy (or C-20-demethyl) ±C-19-dechloro (U.S. Pat. Nos. 4,361,650 and 4,307,016) (prepared by demethylation using Streptomyces or Actinomyces or dechlorination using LAH); and (3) C-20-demethoxy, C-20-acyloxy (—OCOR), ±dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl(demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from Nocardia);

(4) C-15-hydroxy/acyloxy (U.S. Pat. No. 4,364,866) (prepared by the conversion of maytansinol by Streptomyces);

(5) C-15-methoxy (U.S. Pat. Nos. 4,313,946 and 4,315,929) (isolated from *Trewia nudlflora*);

(6) C-18-N-demethyl (U.S. Pat. Nos. 4,362,663 and 4,322,348) (prepared by the demethylation of maytansinol by Streptomyces); and (7) 4,5-deoxy (U.S. Pat. No. 4,371,533) (prepared by the titanium trichloride/LAH reduction of maytansinol).

In order to link the maytansinoid to the cell binding agent, a linking group is used.

Suitable linking groups are well known in the art and include disulfide groups, thioether groups, acid labile groups, photolabile groups, peptidase labile groups and esterase labile groups. Preferred are disulfide groups and thioether groups.

According to the present invention the linking group is part of a chemical moiety that is covalently bound to the maytansinoid through disclosed methods. In a preferred embodiment, the chemical moiety is covalently bound to the maytansinoid via an ester linkage.

Many positions on maytansinoids are expected to be useful as the linkage position, depending upon the type of link. For example, for forming an ester linkage, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

Also preferred is an N-methyl-L-alanine-containing C-3 ester of maytansinol and an N-methyl-L-cysteine-containing C-3 ester of maytansinol or their analogues.

The present invention recites a process for the preparation and purification of a thiol-containing maytansinoid that positions the linking group at C-3 of maytansinol.

Step 1

Synthesis of Maytansinol (2) from an Ester-Bearing Maytansinoid

The first step in the preparation and purification of thiol-containing maytansinoids involves the reductive hydrolysis of a maytansinoid C-3 ester into maytansinol (2).

A) A maytansinoid C-3 ester is dissolved in an anhydrous solvent, then placed under an inert gas atmosphere and cooled.

Preferably, the maytansinoid C-3 ester is maytansine or ansamitocin P-3 (1*c*). Any ansamitocin (1*a–e*), such as ansamitocin P-4, P-3, P-2 and P-1 (described in Asai et al., 35 *Tetrahedron* 1079–1085 (1979); U.S. Pat. No. 4,450,234; Hatano et al., 48 *Agric. Biol. Chem.* 1721–1729 (1984)) can also be used, more preferably ansamitocin P-3 (1*c*). Maytansine can obtained as described by Kupchan et al., 42 *J. Org. Chem.* 2349–2357 (1977). The microbiological preparation of ansamitocin P-3 (1*c*) is described in U.S. Pat. No. 4,450,234 and in Hatano et al., 48 *Agric. Biol. Chem.* 1721–1729 (1984).

Preferably, the anhydrous solvent is tetrahydrofuran (THF), 2-methoxyethyl ether, dioxane or di-ethyl ether, although other solvents can be used. More preferably, the anhydrous solvent is tetrahydrofuran. Preferably, 20 to 30 mL of the anhydrous solvent is used per gram of ester, more preferably 25 mL/g. Preferably, the inert gas is argon, nitrogen or helium, although other gases can be used. More preferably, the inert gas is argon. Preferably, the solution is maintained at between about 0 to −80° C., more preferably between about −30 to −50° C., most preferably between about −35 to −45° C., in a dry ice-acetone bath.

B) A reducing agent is also cooled, and then transferred into the chilled solution of the maytansinoid C-3 ester. The reaction is maintained under an inert gas atmosphere, at a low temperature, and stirred.

Figure 1:
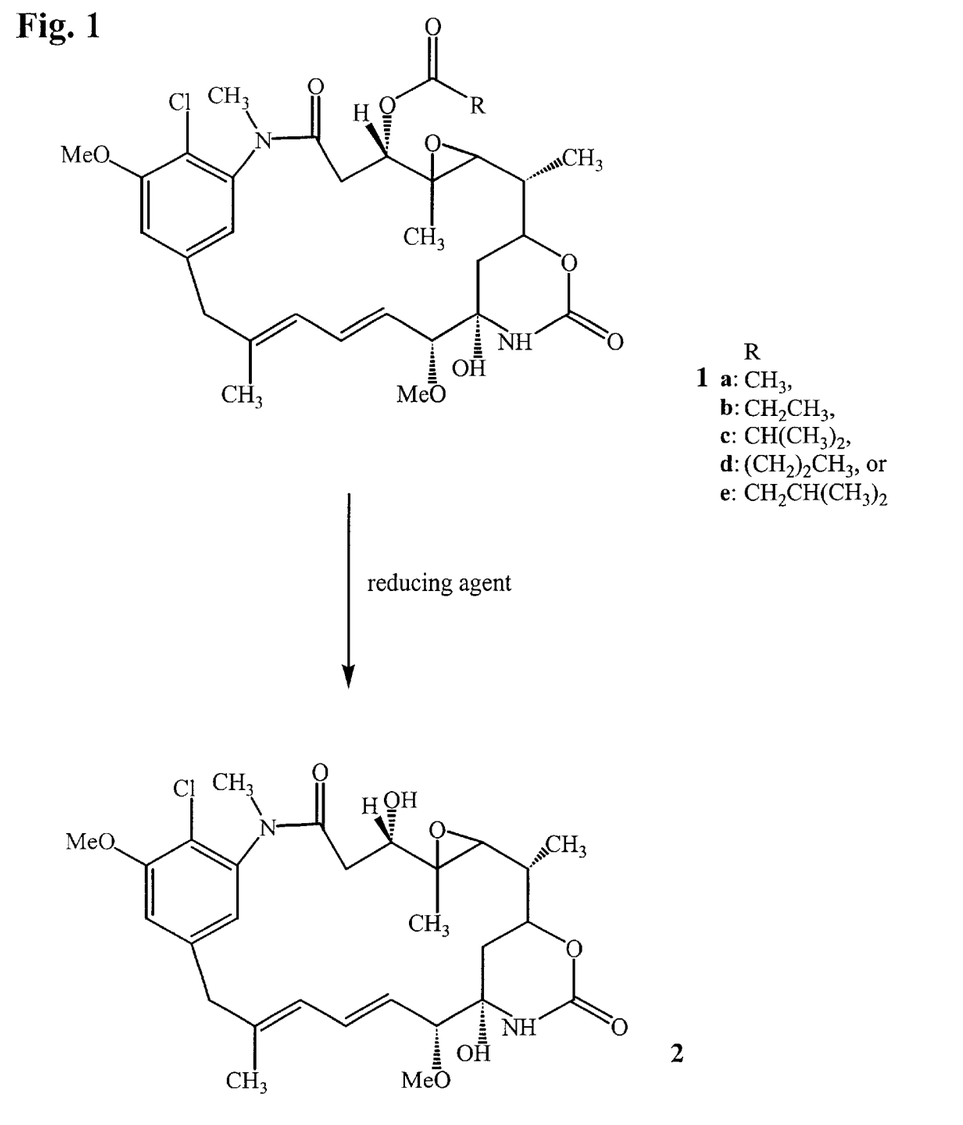
FIG. 1 shows the reduction of ansamitocins 1a–e to yield maytansinol (2).

Preferably, the reducing agent is lithium trimethoxyaluminum hydride (LiAl(OMe)$_3$H), lithium triethoxyaluminum hydride (LiAl(OEt)$_3$H), lithium tripropoxyaluminum hydride (LiAl(OPr)$_3$H), sodium trimethoxyaluminum hydride (NaAl(OMe)$_3$H), sodium triethoxyaluminum hydride (NaAl(OEt)$_3$H) or sodium tripropoxyaluminum hydride (NaAl(OPr)$_3$H). More preferably, the reducing agent is lithium trimethoxyaluminum hydride (LiAl(OMe)$_3$H). Preferably, the reducing agent is cooled to about −30 to −40° C. in a dry ice-acetone bath. Preferably, the cooled reducing agent is transferred into the chilled solution of the maytansinoid C-3 ester via a canula. Preferably, the inert gas is argon, nitrogen or helium, although other gases can be used. More preferably, the inert gas is argon.

Preferably, the reducing agent is used in a concentration of from about 5 to 100 equivalents per mole of the maytansinoid C-3 ester, more preferably from about 7.5 to 30 equivalents per mole, most preferably from about 10 to 20 equivalents per mole. One of ordinary skill in the art will understand that use of reducing agent in amounts greater than about 100 equivalents per mole of the maytansinoid C-3 ester can result in undesired side products. Preferably, the reducing agent is added to the chilled solution of maytansinoid C-3 ester over a time period ranging from about 5 to 40 minutes, more preferably from about 7 to 20 minutes, most preferably from about 8 to 12 minutes. Preferably, the reaction is maintained under an inert gas atmosphere at a temperature range of from about −25° C. to −80° C., more preferably from about −27° C. to −45° C., most preferably from about −30° C. to −35° C. Preferably, the reaction is stirred between about 30 min and three hours, more preferably for about three hours.

One of ordinary skill in the art will understand that the amount of reducing agent used, the temperature maintained during the reaction, the length of the time period over which the reducing agent is added and the reaction time are each dependent on the other. For example, the lower the amount of the reducing agent, the longer the reaction time. Similarly, the lower the temperature, the larger the excess of reducing agent required and the longer the time required for completion of the reaction. Moreover, the slower the rate the reducing agent is added, the longer reaction time required for completion of the reaction.

C) The reaction is quenched, extracted, dried and filtered. The solvent is evaporated under reduced pressure to yield crude maytansinol.

Preferably, the reaction is quenched by the addition of saturated sodium chloride solution, water or ammonium chloride solution, more preferably by the addition of saturated sodium chloride solution. Preferably, the reaction is quenched using between about 20 to 40 mL of the solution per gram of maytansinoid ester used. Preferably, the reaction is extracted with ethyl acetate, dichloromethane, toluene, chloroform or ether, more preferably with ethyl acetate. Preferably, the reaction is extracted at the rate of between about 4×80 to 4×200 mL/g maytansinoid ester used. Preferably, the combined ethyl acetate extracts are dried over sodium sulfate or magnesium sulfate, more preferably sodium sulfate, and filtered.

D) The crude maytansinol (2) may be purified, if required, by chromatography.

In a preferred embodiment, the crude maytansinol (2) may be purified by dissolving it in a minimum volume of ethyl acetate, dichloro methane, ether, chloroform or toluene, more preferably ethyl acetate, and purified via silica gel column chromatography using dichloromethane, chloroform, ethyl acetate or toluene, more preferably dichloromethane. Preferably, the maytansinol (2) is eluted with a step gradient starting with dichloromethane or ethyl acetate, or a mixture of dichloromethane:ethyl acetate:alcohol, chloroform:ethyl acetate or toluene:ethyl acetate, preferably 77:23:0, v/v/v, dichloromethane:ethyl acetate:alcohol. The concentration of alcohol is slowly increased from 0 to about 20%, preferably from 0 to about 10%. Fractions containing the desired product are pooled and evaporated under reduced pressure to yield pure maytansinol (2) as a white solid. The purification may be performed at ambient temperature. Preferably, the purification is performed at a temperature of about 20° C. and 25° C. Preferably, the alcohol is methanol, ethanol, n-propanol, iso-propanol, n-, iso-, sec-, or tert-butanol, more preferably methanol.

In another preferred embodiment, the crude maytansinol (2) may be purified using a cyano-bonded silica HPLC column that is run in normal phase, using organic solvents in the mobile phase. The crude maytansinol (2) is dissolved in ethyl acetate, ethyl acetate:isopropanol:hexane (mobile phase) or in ethyl acetate-isopropanol, preferably ethyl acetate, injected onto the column, and the appropriate peak is collected. Preferably, the cyano-bonded HPLC column that is used for the separation is one having cyanopropyl and cyano-di-isopropyl groups stably bonded to the silica backbone. Such columns are available under the trade names Diazem™, Zorbax™, Monochrom™, and Kromasil™, to name a few. Preferably, the organic solvent used in the mobile phase is hexanes:2-propanol:dichloromethane:ethyl acetate. Preferably, the concentration of each constituent of the organic solvent is in the range 65–75:2–4:15–20:5–10, v/v/v/v, respectively. More preferably, the concentration of each element of the organic solvent is 72:3:18:7, v/v/v/v.

Preferably, maytansinol (2) purified by this process is at least 90% pure, more preferably at least 95% pure. One of ordinary skill in the art will understand that if maytansinol (2) of less than 90% purity is used in the following steps, additional purification steps may be required.

One of ordinary skill in the art will understand that the reduction reaction may yield small amounts of undesired side products, in addition to the maytansinol (2). Thus, purification may be required to remove the contaminants. However, if the side products are not generated, such as where the precise times, temperatures, and amounts are established, then the purification step is not required.

Step 2

Synthesis of Esters of Maytansinol (2) Having a Linking Group

Figure 4:
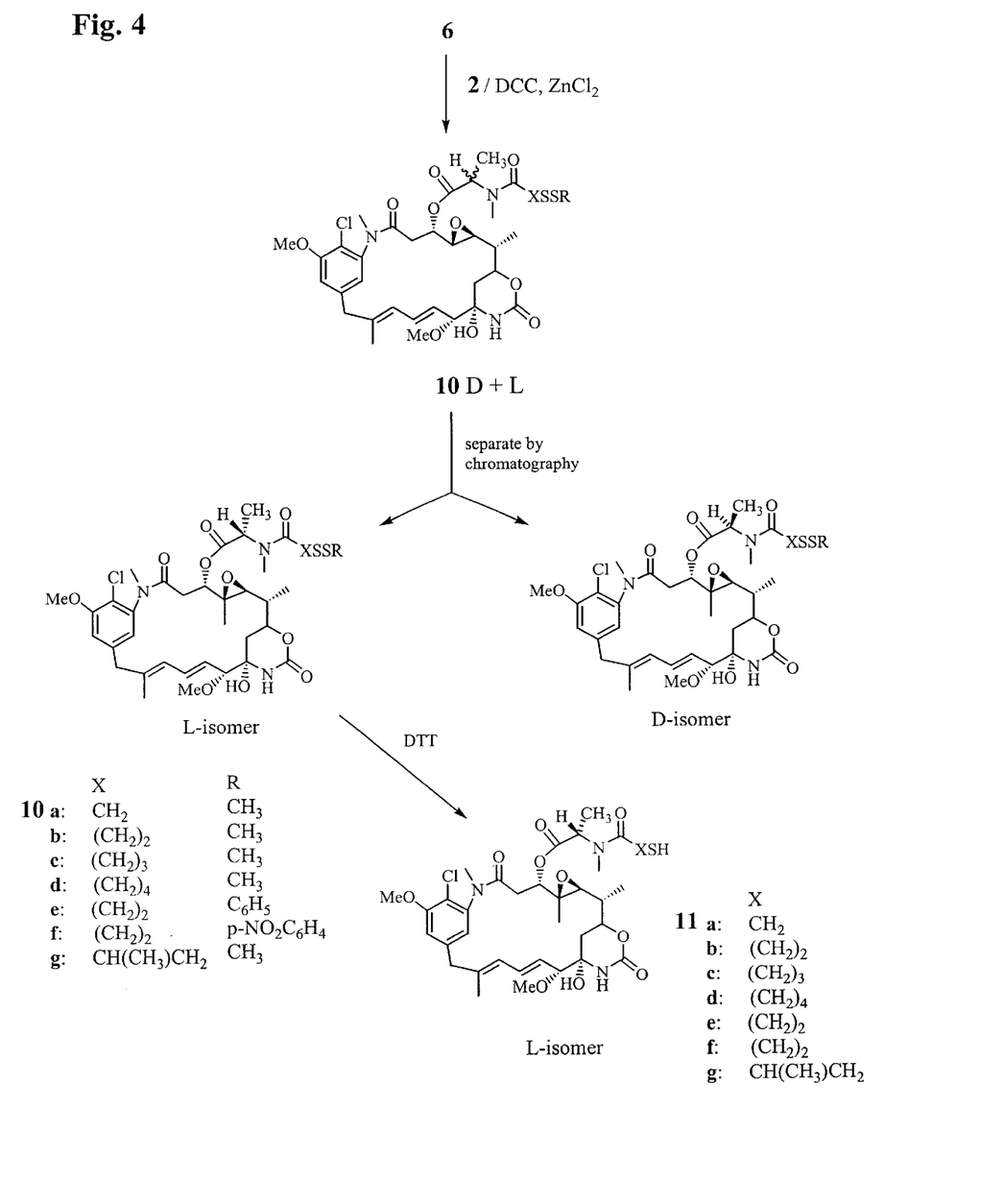
FIG. 4 shows the esterification of maytansinol (2) with the N-methyl-L-alanine derivatives 6a–g containing a disulfide group to yield the disulfide-containing maytansinoid stereoisomers 10, from which the L-isomers are separated via chromatography to yield the disulfide-containing maytansinoid L-isomers 10a–g, which in turn are reduced to yield the thiol-containing maytansinoids 11a–g.
Figure 5:
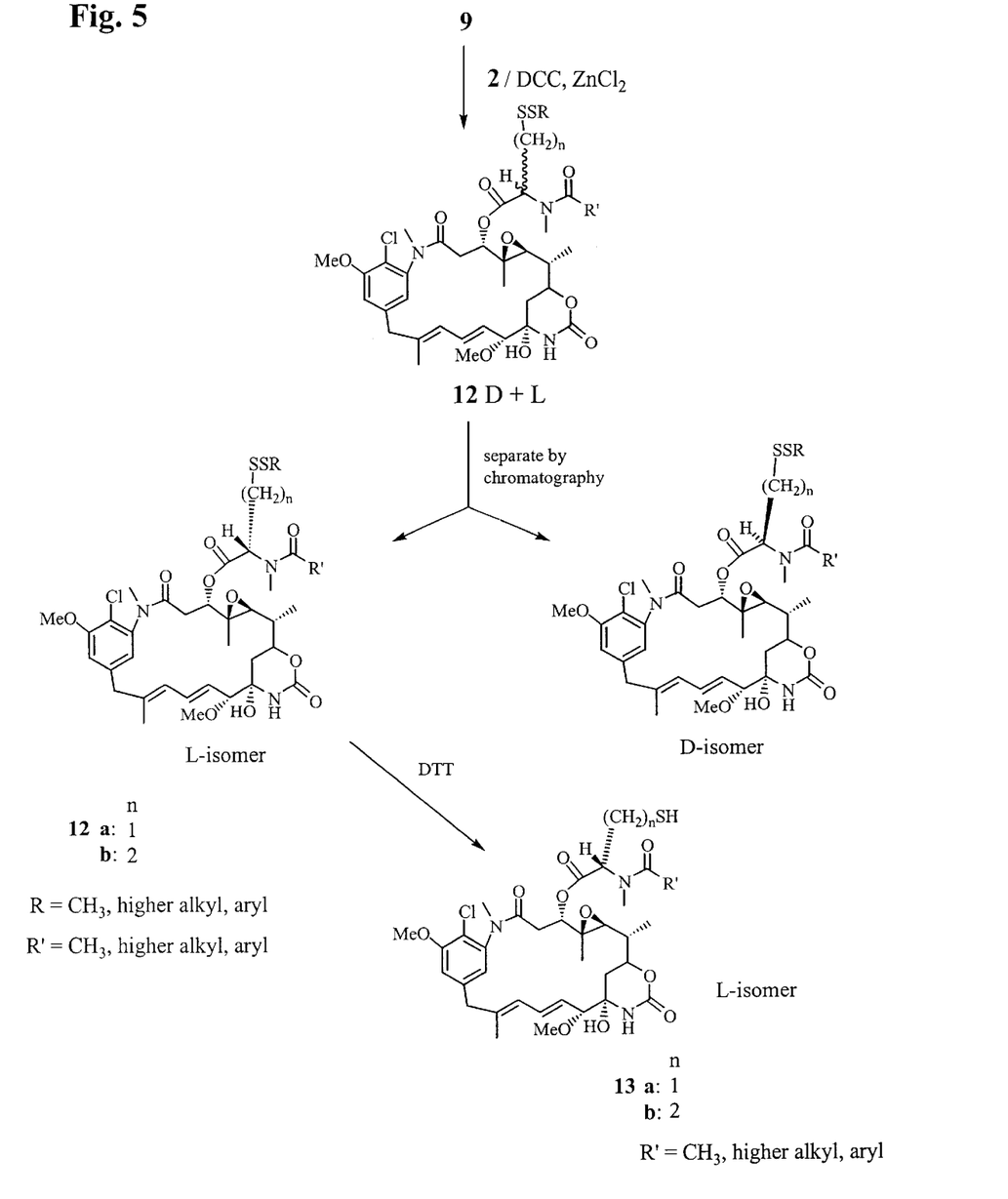
FIG. 5 shows the esterification of maytansinol (2) with the N-methyl-L-cysteine derivatives 9a–b containing a disulfide group to yield the disulfide-containing maytansinoid stereoisomers 12, from which the L-isomers are separated via chromatography to yield the disulfide-containing maytansinoid L-isomers 12a–b, which in turn are reduced to yield the thiol-containing maytansinoids 13a–b.

The maytansinol (2) from Step 1 is next esterified with disulfide-containing N-methyl-L-alanine derivatives 6a–g or N-methyl-L-cysteine derivatives 9a–b, in the presence of dicyclohexylcarbodiimide (DCC) and zinc chloride, to yield L- and D-aminoacyl esters 10a–g and 12a–b of maytansinol, containing a disulfide-linking group. The stereoisomers are then separated, and the L-aminoacyl ester is collected. Because the esterification reaction results in some epimerization at the chiral center of the amino acid derivatives 6a–g and 9a–b, one of ordinary skill in the art will understand that the racemic versions of 6a–g and 9a–b (i.e. a D, L-mixture) can be used in Step 2, in place of the stereoisomers.

A) In one embodiment, the N-methyl-L-alanine derivatives 6a–g containing a disulfide group are produced by the conversion of ω-mercaptocarboxylic acids 3a–e of varying chain lengths into their respective methyl-dithio, e.g. 4a–e (where n=1–4, including branched and cyclic aliphatics), or aryl-dithio, e.g. 5a–b, derivatives by reacting them with methyl methanethiolsulfonate or aryldisulfides, such as diphenyldisulfide, and ring substituted diphenyldisulfides and heterocyclic disulfides, such as 2,2'-dithiopyridine. These carboxylic acids are then reacted with N-methyl-L-alanine to form the desired N-methyl-L-alanine derivatives containing a disulfide group 6a–g that will be condensed with maytansinol (2) to form maytansinoids containing disulfide-linking groups 10a–g.

N-methyl-L-alanine may be prepared as described in the literature (see, Fu, S. J. & Birnbaum, S. M., 75 *J. Amer. Chem. Soc.* 918 (1953)), or is obtainable commercially (Sigma Chemical Company).

Figure 2A:
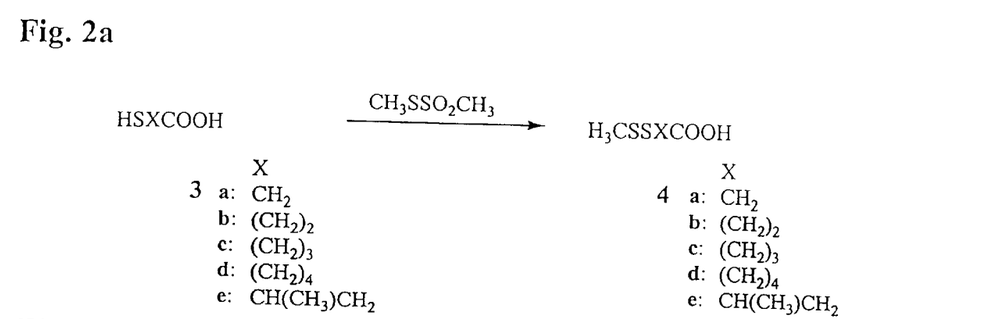
FIG. 2a shows the conversion of the ω-mercaptocarboxylic acids 3a–e to the respective methyl-dithio derivatives 4a–e.
Figure 2B:
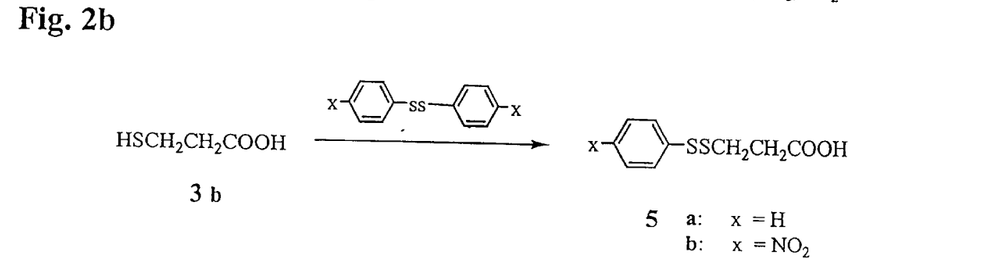
FIG. 2b shows the conversion of the ω-mercaptocarboxylic acid 3b to the respective aryl-dithio derivatives 5a–b.
Figure 2C:
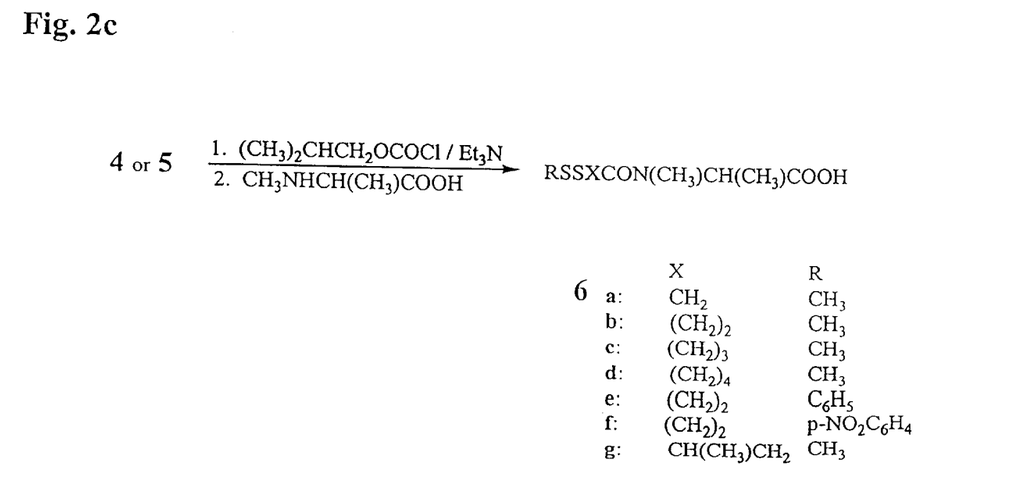
FIG. 2c shows the conversion of the methyl-dithio derivatives 4a–e and the aryl-dithio derivatives 5a–b to N-methyl-L-alanine derivatives 6a–g containing a disulfide group.

Preferably, the N-methyl-L-alanine derivatives containing a disulfide group are N-methyl-N-methyldithioacetyl-L-alanine, N-methyl-N-(3-methyldithio-propanoyl)-L-alanine, N-methyl-N-(4-methyldithio-butanoyl)-L-alanine, N-methyl-N-(3-methyldithio-butanoyl)-L-alanine, N-methyl-N-(5-methyldithio-pentanoyl)-L-alanine, N-methyl-N-(3-phenyldithio-propanoyl)-L-alanine and N-methyl-N-[3-(4-Nitrophenyldithio)-propanoyl]L-alanine.

Figure 3A:
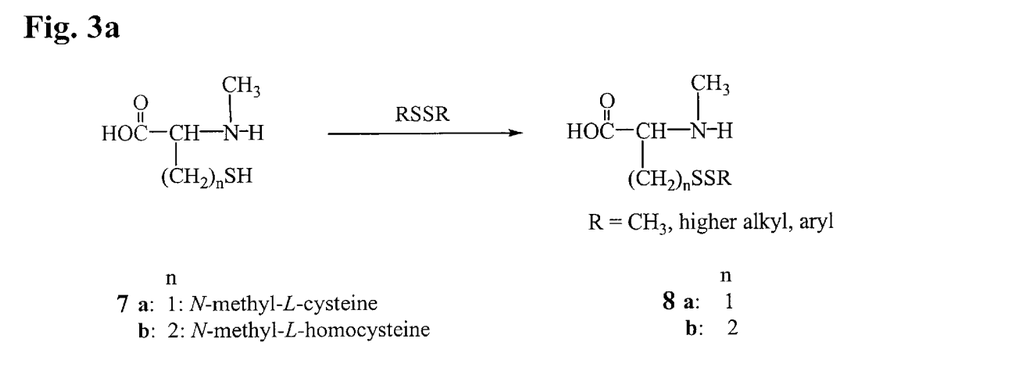
FIG. 3a shows the conversion of N-methylcysteine and N-methylhomocysteine (7a–b) to the respective disulfide derivatives 8a–b.
Figure 3B:
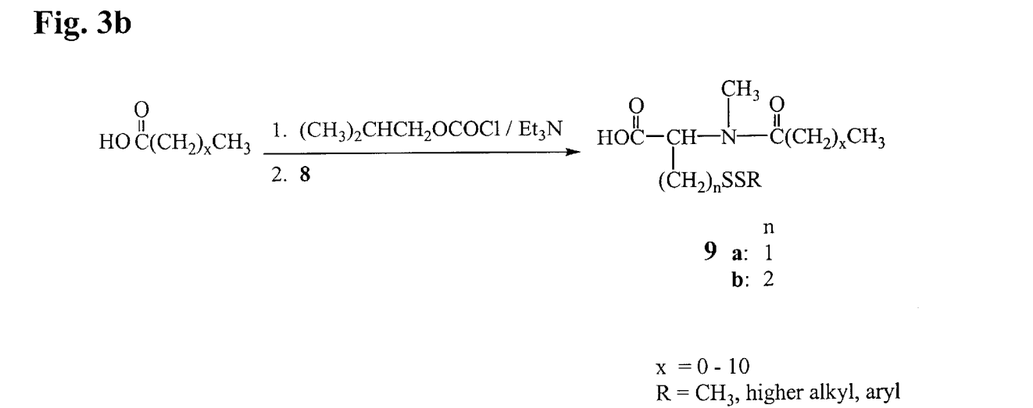
FIG. 3b shows the acylation of the disulfide derivatives 8a–b to N-methyl-L-cysteine derivatives 9a–b containing a disulfide group.

B) In another embodiment, N-methyl-L-cysteine (7a) or N-methyl-L-homocysteine (7b) can be converted to the respective disulfide derivatives 8a–b (n=1 and 2, respectively), which are then acylated to yield the desired N-methyl-L-cysteine or N-methyl-L-homocysteine derivatives containing a disulfide group 9a–b (n=1 and 2, respectively). These disulfide-containing derivatives 9a–b will be condensed with maytansinol (2) to form maytansinoids containing disulfide-linking groups 12a–b.

N-methyl-L-cysteine can be prepared as described in Undheim and Eidem, 23 *Acta Chem. Scand.* 3129–3133 (1970).

Preferably, the N-methyl-L-cysteine derivatives containing a disulfide group are N-acetyl-N-methyl-methyldithiocysteine (9a) and N-acetyl-N-methyl-methyldithiohomocysteine (9b).

C) Maytansinol (2) is esterified with a N-methyl-L-alanine or N-methyl-L-cysteine derivative containing a disulfide group (6a–g and 9a–b) by first preparing a solution of the disulfide-containing derivative. This solution is stirred under an inert gas atmosphere, and treated sequentially with solutions of (a) DCC or EDC ([3-(dimethylamino)propyl]-3-ethylcarbodiimide hydrochloride), preferably DCC, (b) $ZnCl_2$ and (c) maytansinol. The mixture is stirred until completion of the reaction. After the reaction is complete, it is filtered and the filtrate evaporated under reduced pressure yielding a mixture of the L- and D-aminoacyl esters 10 and 12 of maytansinol.

As noted above, because the esterification reaction results in some epimerization at the chiral center of the amino acid derivatives 6a–g and 9a–b, one of ordinary skill in the art will understand that the racemic versions of 6a–g and 9a–b (i.e. a D, L-mixture) can be used in place of the stereoisomers.

Preferably, the N-methyl-L-alanine or N-methyl-L-cysteine derivative containing a disulfide group is N-methyl-N-(methyldithio-propanoyl)-L-alanine (6b) and N-acetyl-N-methyl-methyldithiocysteine (9a), respectively. Preferably, the solution of the disulfide-containing derivative comprises dry methylene chloride, tetrahydrofuran, or ether, preferably dry methylene chloride, using between about 10 to 50 mL/gram maytansinol, preferably 20 mL/gram. Preferably, the inert gas is argon, nitrogen or helium, although other gases can be used. More preferably, the inert gas is argon.

Preferably the DCC or EDC is in methylene chloride, tetrahydrofuran or ether, preferably methylene chloride, using about 10 to 15 mL per gram DCC or EDC, preferably 12 mL/g. Preferably, the DCC or EDC solution is added at the rate of about 5 to 7 moles/mole of maytansinol. Preferably, the $ZnCl_2$ is about 1 M, and it is used at between about 1.2 to 1.5 moles/mole of maytansinol, preferably 1.25 moles, in ether or methylene chloride, preferably ether. Preferably, maytansinol is in methylene chloride, tetrahydrofuran or ether, more preferably methylene chloride, using about 10 to 120 mL solvent per gram of maytansinol, preferably 100 mL/g. The reaction mixture is stirred at between 4 to 30° C., preferably room temperature, for between 1 to 24 hours, preferably three hours. One of ordinary skill in the art will understand that the length of time the reaction requires stirring is dependent on the temperature, with lower temperatures resulting in longer reaction time.

D) Separation of the L- and D-aminoacyl maytansinol esters 10a–g and 12a–b is accomplished via a cyano-bonded silica HPLC column that is run in normal phase, using organic solvents in the mobile phase. A solution of the L- and D-aminoacyl maytansinol ester mixture, dissolved in ethyl acetate or in hexanes:2-propanol:ethyl acetate, is injected on to the column. The mobile phase can be adjusted to obtain separation in retention times of the two isomers that is in excess of 10 minutes.

Alternatively, the separation can be conducted using silica gel chromatography, but the process is not easily converted to an industrial scale. Separation can also be accomplished through other, less desirable, means such as HPLC using chiral columns or silica columns.

Preferably, the cyano-bonded HPLC columns that are used for the separation are those that have cyanopropyl and cyano-di-isopropyl groups stably bonded to the silica backbone. Such columns are available under the trade names Diazem™, Zorbax™, Monochrom™, and Kromasil™, among others. Preferably, the organic solvent used in the mobile phase is hexanes:2-propanol:ethyl acetate. Preferably, the yield of the separation is greater than about 90% and product is at least about 95% pure, more preferably, optically pure. Under the aforementioned conditions, the desired L-isomer has a retention time of about 36 to 46 min, preferably 42 min, while the D-isomer elutes at about 50 to 60 minutes, preferably 56 min. Preferably, the esterification is carried out at about 25° C.

Step 3

Synthesis of Thiol-Containing Maytansinoid 11a–g and 13a–b

To obtain thiol-containing maytansinoids 11a–g and 13a–b, the L-aminoacyl maytansinol esters obtained from Step 2 are dissolved in a solution comprising a solvent and an alcohol. This mixture is stirred under an inert gas atmosphere, and treated with a solution of dithiothreitol or dithioerythritol, in buffer, and containing ethylenediaminetetraacetic acid (EDTA). The progress of the reaction may be monitored by HPLC and is generally complete in 3 h, although it may vary between 1 and 24 h. The completed reaction is treated with a buffered solution containing EDTA, and then extracted. The organic layers are combined, washed and dried. Evaporation of the solvent leaves a residue of crude thiol-containing maytansinoid 11a–g and 13a–b, which may be purified using a preparative cyano-bonded silica HPLC column. Fractions containing the product may be evaporated to yield pure thiol-containing maytansinoid as a white solid.

Preferably, the solvent the L-aminoacyl maytansinol esters obtained from Step 2 are dissolved in is ethyl acetate, dichloromethane or ether, more preferably ethyl acetate, using from about 60 to 80 mL solvent per gram maytansinoid, preferably 72 mL/g. Preferably, the alcohol the L-aminoacyl maytansinol esters obtained from Step 2 are dissolved in is methanol or ethanol, more preferably methanol, using from about 90 to 120 mL alcohol per gram of maytansinoid, preferably 108 mL/g. Preferably, the reaction between L-aminoacyl maytansinol esters and dithiothreitol is in a mixture of ethyl acetate:methanol:aqueous buffer which is capable of keeping the buffer salts, dithiothreitol and maytansinoids (reduced and non-reduced forms) in solution. More preferably, the reaction between L-aminoacyl maytansinol esters and dithiothreitol is in a 1:5:1 mixture of ethyl acetate:methanol:aqueous buffer.

Preferably, the concentration of L-aminoacyl maytansinol esters used in Step 3 is less than about 4 g/L such that the L-aminoacyl maytansinol esters remain solubilized.

Preferably, the reduction reaction is carried out in an oxygen-free atmosphere. Preferably, the inert gas is argon, nitrogen or helium, although other gases can be used. More preferably, the inert gas is argon.

Preferably, the reduction reaction is carried out at between 4 to 30° C., more preferably at room temperature. One of ordinary skill in the art will understand that the reaction can be carried out at lower temperatures, however, the time required for completion of the reaction is increased.

Preferably, the solution containing the L-aminoacyl maytansinol esters is treated with dithiothreitol, dithioerythritol or a phosphine reagent such as tris(2-carboxyethyl) phosphine (TCEP), more preferably dithiothreitol, using about 2 to 3 moles reducing agent per mole maytansinoid, preferably 2.5 moles/mole, in potassium phosphate buffer, sodium phosphate buffer or triethanolamine buffer, preferably potassium phosphate buffer, the buffer at a concentration between about 20 to 100 mM, preferably 50 mM, using 60 to 80 mL of the buffered DTT per gram maytansinoid, preferably 72 mL/g, and containing from about 1 to 10 mM, preferably 2 mM, ethylenediaminetetraacetic acid (EDTA).

Preferably, the completed reaction is treated with a 0.2 M solution of potassium phosphate buffer, sodium phosphate buffer or triethanolamine buffer, more preferably potassium phosphate buffer, using from about 120 to 160 mL buffer per gram maytansinoid, preferably 144 mL/g, and containing from about 1 to 10 mM, preferably 2 mM, EDTA. Preferably, the extraction is with ethyl acetate, dichloro methane, or ether, more preferably ethyl acetate, using 200 to 500 mL per gram maytansinoid, preferably 300 mL/g, repeated three times. Preferably, the combined organic layers are washed with a saturated sodium chloride solution, water or a saturated ammonium chloride solution, more preferably a saturated sodium chloride solution, using 40 to 100 mL per gram maytansinoid, preferably 50 mL/g, and then dried over sodium sulfate or magnesium sulfate, preferably sodium sulfate.

Preferably, the cyano-bonded HPLC columns that are used for the separation are those that have cyanopropyl and cyano-di-isopropyl groups stably bonded to the silica backbone. Such columns are available under the trade names Diazem™, Zorbax™, Monochrom™, and Kromasil™, to name a few. More preferably, a Diazem preparative CN column (250 mm×50 mm, 10 micron particle size) is used. Preferably, the organic solvent used in the mobile phase is hexanes:2-propanol:ethyl acetate. More preferably, the organic solvent used in the mobile phase is a 78.0:5.5:16.5 (v/v/v) mixture of hexanes:2-propanol:ethyl acetate. Preferably, the flow rate is 150 mL/min. Preferably, the yield of the separation is greater than 75%, and product is at least about 90% pure, more preferably, at least about 95% pure. Preferably, the desired thiol-containing maytansinoids 11a–d and 13a–b have a retention time of 16 min, within a range from about 14 to 18 min.

Specific examples of N-methyl-L-alanine-containing maytansinoid derivatives taught by the present invention are represented by formulas (I)–(IV):

(I)

wherein: Z represents H or SR, wherein R represents a methyl, linear alkyl, branched alkyl, cyclic alkyl, simple or substituted aryl or heterocyclic group; l represents an integer of 1 to 10; and may represents a maytansinoid.

(II)

wherein: $R_1$ and $R_2$, which may be the same or different, represents H, $CH_3$ or $CH_2CH_3$; Z represents H or SR, wherein R represents methyl, linear alkyl, branched alkyl, cyclic alkyl, simple or substituted aryl, or heterocyclic; m represents 0, 1, 2 or 3; and may represents a maytansinoid.

(III)

wherein: Z represents H or SR, wherein R represents methyl, linear alkyl, branched alkyl, cyclic alkyl, simple or substituted aryl, or heterocyclic; p represents an integer of 3 to 8; and may represents a maytansinoid.

(IV)

wherein: Z represents H or SR, wherein R represents methyl, linear alkyl, branched alkyl, cyclic alkyl, simple or substituted aryl or heterocyclic; q represents an integer from 1 to 10; Y represents Cl or H; and X represents H or CH$_3$.

Specific examples of N-methyl-L-cysteine-containing maytansinoid derivatives useful in the present invention are represented by formulas (V) and (VI):

(V)

wherein: Z represents H or SR, wherein R represents methyl, linear alkyl, branched alkyl, cyclic alkyl, simple or substituted aryl, or heterocyclic; o represents 1 or 2; q represents 0 or an integer of 1 to 10; and may represents a maytansinoid.

(VI)

wherein: Z represents H or SR, wherein R represents methyl, linear alkyl, branched alkyl, cyclic alkyl, simple or substituted aryl or heterocyclic; o represents 1 or 2; q represents 0 or an integer of 1 to 10; Y represents Cl or H; and X represents H or CH$_3$.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as Cl, Br, F, nitro groups, amino groups, sulfonic acid groups, carboxylic acid groups, hydroxy groups and alkoxy groups.

Examples of heterocyclics are compounds wherein the heteroatoms are selected from O, N and S, and include pyrrollyl, pyridyl, furyl and thiophene.

DEFINITIONS

As used herein, the terms "room temperature" and "ambient temperature" mean environmental temperature or uncontrolled temperature. The term "optical purity" means that the purity exceeds 98%. Where ranges are specified herein, e.g. temperature, time, concentration etc., the range includes all specific values within the range, as well as subranges falling within the broad range. Where values are stated to be "about" a specific value, or range of values, it is to be understood that statistically insignificant variations in those values are included as well.

EXAMPLES

The invention will now be illustrated by reference to non-limiting examples. Unless otherwise stated, all percents, ratios, parts, etc. are by weight.

Example 1
Synthesis of Thiol-Containing Maytansinoid Derivatives

Melting points were determined on a electrothermal melting point apparatus. Proton magnetic resonance ($^1$H NMR) spectra were obtained on a Varian™ EM360 spectrometer at 60 MHz or on a Bruker™ AM300 machine at 300 MHz. Chemical shifts are reported in δ values relative to an internal tetramethylsilane (TMS) standard. UV spectra were recorded on a Perkin Elmer™ λ4A spectrophotometer. Optical rotations were determined using a Perkin Elmer™ model 241 polarimeter. A Rainin™ HP, Hewlett Packard™, or Hitachi™ instrument equipped with wavelength or diode array UV detector and a Waters™ Radialpak C-18 column or Diazem™ cyano or Chromasil™ cyano column was used for HPLC analyses and purification. Elemental analyses were performed by Atlantic Microlabs, Atlanta, GA.

2-Mercaptoacetic acid (3a), 3-mercaptopropanoic acid (3b) and 4-mercaptobutanoic acid (3c) are commercially available.

5-Mercaptopentanoic acid (3d). 5-Mercaptopentanoic acid (3d) was prepared by a modification of a literature method (Khim et al, 37 J. Org. Chem. 2714–2720 (1972)). To a stirred solution of 5-bromopentanoic acid (1.80 g, 0.01 mol) in absolute ethanol (25 mL) was added thiourea (0.761 g, 0.01 mol) and the reaction mixture was refluxed for 6 hours. A solution of 50% aqueous NaOH (20 mL) was then added and the mixture refluxed for an additional two hours. The mixture was then diluted with water (100 mL), acidified (aqueous HCl), and extracted with ethyl acetate (4×50 mL). The combined organic layers were dried over sodium sulfate and evaporated under reduced pressure. The residue was chromatographed over silica gel eluting with methylene chloride/ethyl acetate to give 0.885 g (66%) of a colorless liquid. $^1$H NMR (CDCl$_3$) δ1.3 (1H, t), 1.6 (4H, m), 2.4 (4H, m), 11.5 (1H, s).

3-Mercaptobutanoic acid (3e). A solution of the commercially available β-butyrolactone (3.0 g, 35.0 mmol) in tetrahydrofuran (20 mL) was added to di-isopropylethyl amine (10.0 g, 77.5 mmol). The reaction mixture was stirred under an argon atmosphere, and treated with thioacetic acid (3.0 g, 39.0 mmol). The reaction mixture was stirred at room temperature for 6 h. The solvent was then evaporated and the product purified by column chromatography over silica gel, eluting with ethyl:hexanes (3:1, v/v) containing 3% acetic acid. The thioacetate derivative of 3e was obtained as a colorless oil (2.0 g, 35% yield). $^1$H NMR (CDCL$_3$): δ1.5 (3H, d), 2.3 (3H, s), 2.8 (2H, d), 4.0 (1H, m) and 11.3 (1H, s). The thioacetate was converted into the thiol 3e by base hydrolysis. A solution of the thioacetate (1.5 g, 9.3 mmol) in methanol (6 mL) was treated with a solution of 3.3 M sodium hydroxide in water (10 mL). The reaction was stirred under an argon atmosphere. The progress of the reaction was monitored by TLC, and was judged complete in 3 h. The reaction mixture was acidified by addition of 1 M hydrochloric acid (40 mL), and extracted with ethyl acetate (70 mL). The organic extract was dried over sodium sulfate, filtered, and evaporated under reduced pressure to give 3-mercaptobutanoic acid (3e), which was used without further purification for the synthesis of 4e.

Methyldithio-acetic acid (4a). To a stirred solution of mercaptoacetic acid (3a) (3.0 g, 0.0326 mmol) in water (100 mL), cooled in an ice bath, was added methyl methanethiosulfonate (4.52 g, 0.036 mol) in absolute ethanol (40 mL). The reaction mixture was allowed to warm to room temperature and stirred overnight. The reaction mixture was then diluted with saturated, aqueous NaCl (300 mL), and extracted with diethyl ether (3×100 mL). The combined organic layer was washed with saturated sodium chloride (100 mL), and dried over Na$_2$SO$_4$, and filtered. The filtrate was evaporated under reduced pressure, and the residue distilled under vacuum to yield 4a as a colorless oil (2.90 g, 64% yield) bp$_{1mm}$=100° C. $^1$H NMR: δ2.4 (3H, s), 3.5 (3H, s) and 10.2 (1H, s).

3-Methyldithio-propanoic acid (4b). To a stirred solution of 3-mercaptopropanoic acid (3b) (5.00 g. 0.047 mol) in water (150 mL), cooled in an ice bath, was added methyl methanethiosulfonate (6.54 g. 0.052 mol) in absolute ethanol (75 mL). The reaction mixture was stirred overnight at room temperature. The mixture was then diluted with saturated, aqueous NaCl (400 mL) and extracted with ether (3×150 mL). The combined ether extracts were washed with saturated NaCl, dried over Na$_2$SO$_4$ and concentrated. The residue was distilled to afford a colorless liquid (6.47 g, 90% yield): bp$_{1.0}$105° C. $^1$H NMR (CDCl$_3$) δ2.3 (3H, s), 2.8 (4H, m), 11.2 (1H, s).

4-Methyldithio-butanoic acid (4c). To a stirred solution of bis-(3-carboxypropyl)-disulfide (1.00 g, 4.20 mmol) in methanol (20 mL) was added a solution of dithiothreitol (0.647 g, 4.20 mmol) in H$_2$O (20 mL). A solution of 10M NaOH (0.842 mL, 8.42 mmol) was then added and the mixture was allowed to stir at room temperature overnight to effect complete reduction. Methyl methanethiolsulfonate (1.17 g, 9.24 mmol) was added and the reaction mixture allowed to stir for another three hours. The mixture was then diluted with saturated, aqueous NaCl (150 mL), acidified (aqueous HCl), and extracted with ethyl ether (3×100 mL). The combined organic layers were washed with saturated NaCl, dried (Na$_2$SO$_4$), concentrated and the concentrate was chromatographed on silica gel eluting with methylene chloride/ethyl acetate to give 0.867 g (56%) of a clear liquid. $^1$H NMR (CDCl$_3$) δ2.1 (2H, m), 2.4 (3H, s), 2.4 (2H, m), 2.7 (2H, m), 11.1 (1H, s).

5-Methyldithio-pentanoic acid (4d). To a stirred solution of 5-mercaptopentanoic acid (3d) (0.500 g, 3.73 mmol) in water (20 mL) was added a solution of methyl methanethiosulfonate (0.517 g, 4.10 mmol) in absolute ethanol (5 mL) and the mixture was stirred at room temperature for 3 hours. The mixture was then diluted with aqueous, saturated NaCl (100 mL) and extracted with ethyl ether (3×100 mL). The combined organic layers were washed with saturated NaCl, dried (Na$_2$SO$_4$), evaporated under reduced pressure and the concentrate was chromatographed over silica eluting with methylene chloride/ethyl acetate to yield 0.602 g (90%) white crystals: mp 42–44° C. $^1$H NMR (CDCl$_3$) δ1.7 (4H, m), 2.4 (3H, s), 2.4 (2H, m), 2.7 (2H, m), 11.1 (1H, s).

3-Methyldithio-butanoic acid (4e). A solution of 3e (1.1 g, 9.3 mmol) in ethyl acetate (10 mL) was treated sequentially with di-isopropylethyl amine (3.4 g, 27 mmol) and a solution of methyl methanethiosulfonate (1.5 g, 12.0 mmol) in absolute ethanol (8 mL). The reaction mixture was stirred at room temperature under argon for 3 h. The solvent was then evaporated, and the residue treated with 3 M hydrochloric acid (15 mL) and extracted with ethyl acetate (40 mL). The organic layer was separated, dried over sodium sulfate, filtered and evaporated. The residue was purified by column chromatography over silica gel, eluting with ethyl acetate-:hexanes (3:1, v/v) containing 3% acetic acid. The product 4e was obtained as a colorless oil (0.61 g, 40% yield). $^1$H NMR (CDCl$_3$): δ1.4 (3H, d), 2.3 (3H, s), 2.8 (2H, d), 3.9 (1H, m) and 11.5 (1H, s).

3-Phenyldithio-propanoic acid (5a). To a stirred solution of diphenyl disulfide (3.0 g, 13.8 mmol) in a mixture of ether (10 mL) and methanol (20 mL), under a nitrogen atmosphere, at room temperature was added a solution of 3-mercaptopropanoic acid (3b) (0.49 g, 4.6 mmol) in ether (5 mL), followed by a solution of 10M NaOH (0.46 mL, 4.6 mmol). The reaction mixture was stirred at room temperature for 20 hours, then stripped of the solvents under reduced pressure. The product was purified by column chromatography on silica gel eluting with ethyl acetate/hexane. The product was obtained as a white solid (0.56 g, 56.6%), mp 57–59° C. $^1$H NMR (CDCl$_3$, TMS) δ2.6–3.0 (4H, m), 7.1–7.6 (5H, m), 10.6 (1H, s).

3-(4-Nitrophenyldithio)-propanoic acid (5b). To a stirred solution of bis-(4-nitrophenyl)-disulfide (3.00 g, 9.73 mmol) dissolved in a mixture of THF (200 mL) and methanol (50 mL) was added 3-mercaptopropanoic acid (3b) (0.688 g, 6.49 mmol). One drop of a solution of 10 N NaOH was then added to the mixture and the reaction stirred for one hour. The reaction mixture was then diluted with saturated NaCl (100 mL) and extracted with ethyl acetate (3×75 mL). The combined organic layers were dried over sodium sulfate, evaporated under reduced pressure and the product was chromatographed over silica gel eluting with methylene chloride/ethyl acetate to yield 0.885 g (53%) of a light yellow solid; mp 98–100° C. $^1$H NMR (CDCOCD$_3$) δ2.8 (2H, m), 3.1 (2H, m), 7.8 (2H, d), 8.2 (2H, d).

N-methyl-N-methyldithioacetoyl-L-alanine (6a). To a stirred solution of 1-(3-dimethylaminopropyl)-3-ethylcarbodiimide hydrochloride (2.99 g, 15.6 mmol) and triethylamine (1.58 g, 15.6 mmol) in dry CH$_2$Cl$_2$ (40 mL) at 0° C. was added a solution of methyldithio-acetic acid (Singh et al., 104 *Anal. Biochem.* 51–58 (1980) (4a) (1.66 g, 12.0 mmol) in dry CH$_2$Cl$_2$ (20 mL). A solution of 4-dimethylaminopyridine (0.073 g, 0.60 mmol) in dry CH$_2$Cl$_2$ (2 mL) was added and the mixture stirred for 45 min. at 0° C. A mixture of N-methyl-L-alanine (0.619 g, 6.00 mmol) and triethylamine (0.607 g, 6.00 mmol) in dry DMF (30 mL) was then added and the mixture stirred at 0° C. for two hours. The reaction mixture was diluted with water (100 mL), stirred for another thirty minutes, then acidified (aqueous HCl) and extracted with ethyl acetate (4×75 mL). The combined organic layers were washed several times with water, dried over $Na_2SO_4$, and evaporated under reduced pressure. The residue was chromatographed over silica gel eluting with methylene chloride ethyl acetate to yield 0.25 g (19%) of a pale yellow oil. $^1$H-NMR ($CDCl_3$) δ1.4 (3H, d), 2.4 (3H, s), 2.9, 3.0 (total 3H, 2s), 3.6 (2H, s), 4.7, 5.2 (total 1H, 2q), 9.8 (1H, s).

N-methyl-N-(3-methyldithio-propanoyl)-L-alanine (6b). To a stirred solution of 3-methyldithio-propanoic acid (4b) (1.00 g, 6.57 mmol) in dry THF (20 mL) at −10° C. under argon was added isobutylchloroformate (0.897 g, 6.57 mmol) and triethylamine (0.665 g, 6.57 mmol) and the reaction mixture was stirred for 15 minutes. A mixture of N-methyl-L-alanine (0.677 g, 6.57 mmol) and triethylamine (1.33 g, 13.14 mmol) in water (10 mL) was added and the reaction mixture was stirred at room temperature overnight. The mixture was then diluted with water (50 mL), acidified (aqueous HCl), and extracted with ethyl acetate (4×50 mL). The combined organic layers were dried over sodium sulfate, the solvent evaporated under reduced pressure and the residue chromatographed over silica gel eluting with methylene chloride/ethyl acetate to yield 0.556 g (34%) white crystals: mp 98–100° C. $^1$H NMR ($CDCl_3$) δ1.3 (3H, d), 2.2 (3H, s), 2.7 (4H, m), 4.5 (1H, q), 10.7 (1H, s). Anal. calculated for $C_8H_{15}NO_3S_2$:C, 40.49; H, 6.37; N, 5.90; mol wt. 237.33. Found: C, 40.42; H, 6.41; N, 5.93.

N-methyl-N-(4-methyldithio-butanoyl)-L-alanine (6c). To a stirred solution of 4-methyldithio-butanoic acid (4c) (0.200 g, 1.20 mmol) in dry THF (10 mL) at −20° C. under argon was added isobutyl chloroformeta (0.164 g, 1.20 mmol) and triethylamine (0.121 g, 1.20 mmol) and the mixture was stirred for twenty minutes. A mixture of N-methyl-L-alanine (0.124 g, 1.20 mmol) and triethylamine (0.243 g, 2.40 mmol) in water (5 mL) was then added and the reaction mixture was stirred at room temperature for five hours. The reaction mixture was then treated as described above for 6b giving the title compound as white crystals (0.135 g, 44%): mp 92–93° C. $^1$H NMR ($CDCl_3$) δ1.4 (3H, d), 2.0 (2H, m), 2.3 (3H, s), 2.7 (4H, m), 2.9 (3H, s), 5.1 (1H, q), 10.5 (1H, s).

N-methyl-N-(5-methyldithio-pentanoyl)-L-alanine (6d). To a stirred solution of 5-methyldithio-pentanoic acid (4d) (0.202 g, 1.12 mmol) in dry THF (15 mL) at −40° C. under argon was added isobutyl chloroformate (0.153 g, 1.12 mmol) and triethylamine (0.113 g, 1.12 mmol) and the reaction mixture was stirred for 20 minutes at −10° C. A solution of N-methyl-L-alanine (0.116 g, 1.12 mmol) and triethylamine (0.227 g, 2.24 mmol) in water (5 mL) was then added and the mixture was stirred at 0° C. for five hours. The reaction mixture was treated as described above for 6b affording the title compound as white crystals (0.196 g, 66%): mp 84° C. $^1$H NMR ($CDCl_3$) δ1.4 (3H, d), 1.8 (4H, m), 2.4 (3H, s), 2.7 (4H, m), 3.0 (3H, s), 5.2 (1H, q), 10.7 (1H, s).

N-Methyl-N-(3-phenyldithio-propanoyl)-L-alanine (6e). A solution of 3-phenyldithio-propanoic acid (5a) (1.8 g, 8.4 mmol) in dry THF was stirred vigorously under a nitrogen atmosphere and cooled to −15° C. Isobutyl chloroformate (1.2 mL, 9.25 mmol) and triethylamine (1.29 mL, 9.25 mmol) were added and the reaction mixture was stirred at this temperature for ten minutes. A solution of N-methyl-L-alanine (0.87 g, 8.4 mmol) and triethylamine (1.29 mL, 9.25 mmol) in water (10 mL) was then added and the reaction mixture was stirred for fifteen minutes at −15° C. and then warmed to room temperature and stirred for an additional period of 2.5 hours. 1 M HCl (10 mL) was added and the reaction mixture was extracted with ethyl acetate (4×50 mL). The combined organic layers were dried with $Na_2SO_4$, filtered, and evaporated under reduced pressure. The crude mixture was purified by column chromatography on silica gel eluting with ethyl acetate/hexane-containing 2% acetic acid to give 6e a white solid (1.5 g, 60%): mp 96–97° C. $^1$H NMR ($CDCl_3$/TMS) δ1.4 (2H, d), 2.7–3.0 (7H, m), 5.2 (1H, q), 7.2–7.6 (5H, m).

N-Methyl-N-[3-(4-nitrophenyldithio)-propanoyl]-L-alanine (6f). To a stirred solution of 3-(4-nitrophenyldithio)-propanoic acid (5b) (0.100 g, 0.386 mmol) in dry THF (10 mL) at −40° C. under argon was added isobutyl chloroformate (0.053 g, 0.386 mmol) and triethylamine (0.039 g, 0.38 mmol) and the reaction stirred at 0° C. for one hour. An aqueous solution (5 mL) of N-methyl-L-alanine (0.040 g, 0.386 mmol) and triethylamine (0.039 g, 0.386 mmol) was then added and the mixture stirred at 0° C. for five hours. The mixture was diluted with water (50 mL), acidified (aqueous HCl), and extracted with ethyl ether (3×25 mL). The combined organic layers were dried ($Na_2SO_4$), and the solvent evaporated under reduced pressure. The residue was chromatographed over silica gel eluting with methylene chloride/ethyl acetate to yield 0.048 g (36%) yellow crystals: mp 74–77° C. $^1$H NMR ($CDCl_3$) δ1.4 (3H, d), 2.6–3.4 (4H, m), 2.9 (3H, s), 5.1 (1H, q), 7.6–8.3 (4H, 2d).

N-Methyl-N-(3-methyldithio-butanoyl)-L-alanine (6g). A solution of 4e (3.52 g, 21.2 mmol) in tetrahydrofuran (20 mL) was cooled to −20° C., and stirred under an argon atmosphere. Isobutylchloroformate (3.48 mL, 21.2 mmol) and triethyl amine (3.7 mL, 25.4 mmol) were then added. The reaction mixture was stirred at −20° C. for 15 min. A solution of N-methyl-L-alanine (2.74 g, 26.6 mmol) in water (5 mL) and triethylamine (7.4 mL, 50.8 mmol) was added and the reaction warmed to room temperature and stirred for 2 h. The reaction mixture was diluted with water (100 mL) and acidified to pH of 2 by addition of 1M HCl. The product was extracted with ethyl acetate (5×50 mL). The combined organic layer was dried with sodium sulfate, filtered and evaporated. The residue was purified by column chromatography over silica gel eluting with ethyl acetate:hexanes (1:1, v/v) to give pure 6g as a white solid (0.69 g, 12% yield). $^1$H NMR ($CDCl_3$): δ1.3 (3H, d), 1.5 (3H, d), 2.41 (3H, s), 2.8 (2H, m), 3.0 (3H, s), 3.5 (1H, m) and 5.3 (1H, m).

Methyldithio-N-methylcysteine (8a). A solution of N-methylcysteine (7a) (Undhein, K., & Eidem, A., 23 *Acta Chem. Scandinavica* 3129–3133 (1970)) (1.5 g, 11.1 mmol) in $H_2O$ (20 mL) was stirred at room temperature, under an atmosphere of argon, and treated with a solution of methyl methanethiol sulfonate (3.0 mL, 29.2 mmol) in ethanol (10 mL). The reaction mixture was stirred at this temperature for two hours and then diluted with $H_2O$ (100 mL) and washed with ether (4×40 mL). The aqueous layer was acidified to pH 2 and passed through an Amberlite IRA 93 (—OH form) column. The column was washed with water and the effluent was collected and evaporated to dryness under reduced pressure to give a white solid (1.2 g, 60%), mp 194–195° C. $^1$H NMR ($D_2O$, TMS ext. standard): δ2.2(3H,s), 2.5(3H,s), 3.2(2H,d), 3.7(1H,q).

Methyldithio-N-methylhomocysteine (8b). One of ordinary skill in the art would understand how to make methyldithio-N-methylhomocysteine (8b) based on the method for making methyldithio-N-methylcysteine (8a).

N-methylhomocysteine (7b) can be made by the method previously described for N-methylcysteine (Undhein, K., & Eidem, A., 23 *Acta Chem. Scandinavica* 3129–3133 (1970)).

N-Acetyl-N-methyl-methyldithiocysteine (9a). To a solution of glacial acetic acid (0.25 mL, 4.4 mmol) in dry THF (4 mL), at −20° C. under an atmosphere of $N_2$ were added, with stirring, isobutylchloroformate (0.57 mL, 4.4 mmol) and triethylamine (0.61 mL, 4.4 mmol). The reaction mixture was stirred at this temperature for 20 minutes and then treated with a solution of methyldithio-N-methylcysteine (8a) (0.4 g, 2.2 mmol) and triethylamine (0.45 mL, 3.3 mmol) in $H_2O$ and then allowed to stir overnight. The mixture was then diluted with water (25 mL) and acidified to pH 2 with HCl and extracted with ethyl acetate (4×50 mL). The combined organic layer was dried with sodium sulfate and the solvent evaporated under reduced pressure to give the product as a pale yellow solid (0.2 g, 55%) mp 137–138° C. $^1$H NMR (CDCl$_3$): δ2.1(3H,s), 2.3(3H,s), 3.0(3H,s), 3.2(2H,d) and 4.8(1H,q).

N-acetyl-N-methyl-methyldithiohomocysteine (9b). One of ordinary skill in the art will understand how to make N-acetyl-N-methyl-methyldithiohomocysteine (8b) based on the method for making N-acetyl-N-methyl-methyldithiocysteine (9a).

Step 1
Reduction of Ansamitocin P-3 (1c) into Maytansinol

Ansanmitocin P-3 (1c) was converted into maytansinol (2) by reductive hydrolysis. Ansamitocin P-3 (1c) (3.2 g, 5.0 mmol) was dissolved in anhydrous THF (80 mL), and the solution was placed under an argon atmosphere, and cooled in a dry ice-acetone bath to −40° C.

To a separate flask was added a solution of lithium aluminum hydride (75 mmol, 75 mL of a 1.0 M solution in THF). The solution was placed under an argon atmosphere and cooled to −40° C. A solution of anhydrous methanol (9.1 mL, 225 mmol) in THF (40 mL) was added dropwise using a dropping funnel. The temperature was maintained between −30 and −40° C., and, after the addition was complete, the reaction mixture was stirred for an additional period of 10 min. The resulting solution of lithium trimethoxyaluminum hydride (LiAlH(OMe)$_3$H) was transferred via a canula over 10 min. into the chilled solution of ansamitocin P-3 (1c). The reaction temperature was maintained between −30 and −35° C. under argon, and stirred for 1 h.

The reaction was quenched by the addition of saturated sodium chloride solution (100 mL), and extracted with ethyl acetate (4×400 mL). The combined ethyl acetate extracts were dried over sodium sulfate and filtered. The solvent was evaporated under reduced pressure to give crude maytansinol (2).

The crude product was dissolved in ethyl acetate and loaded onto a silica gel column packed in dichloromethane. The column was eluted with a step gradient starting with a mixture of dichloromethane:ethyl acetate:methanol (77:23:0, v/v/v) and slowly increasing the concentration of methanol from 0% to 10%. Fractions containing the desired product were pooled and evaporated under reduced pressure to give pure maytansinol (71% yield) as a white solid.

The maytansinol was further purified by HPLC as follows. A Kromasil™ cyano preparative HPLC column (250 mm×50 mm, 10 micron particle size) was equilibrated in a mixture of hexanes:2-propanol:dichloromethane:ethyl acetate (72:3:18:7, v/v/v) at a flow rate of 150 mL/min. A solution of the maytansinol was injected onto the column. Under these conditions, the maytansinol has a retention time of 22 min and a purity of >98%.

Step 2
Esterification of Maytansinol (2) with N-methyl-N-methyldithioacetoyl-L-alanine (6a)

A solution of N-methyl-N-methyldithioacetoyl-L-alanine (6a) (4.2 mg, 0.017 mmol) in dichloromethane (0.1 mL) was stirred under an argon atmosphere, and treated sequentially with a solution of maytansinol (2 mg, 0.0035 mmol) in dichloromethane (0.2 mL), DCC (4.4 mg) in dichloromethane (0.2 mL) and 1M zinc chloride (0.0035 mmol) in ether. The reaction was stirred for 75 min. The reaction mixture was then filtered and the solvent was evaporated. The residue was purified by preparative TLC on silica gel, using 6% methanol in chloroform to give the desired L-maytansinoid ester 10a.

The compound 10a can be more efficiently purified using a Diazem™ cyano HPLC column (250 mm×10 mm, 10 micron particle size) equilibrated in a mixture of hexanes:2-propanol:ethyl acetate (17:2:6, v/v/v) at a flow rate of 4.7 mL/min. $^1$H NMR (CDCl$_3$) L-aminoacyl isomer (10a): δ0.90(3H, s), 1.3 (6H, d,d) 1.46–1.52 (1H, m), 1.60 (3H, s), 2.30 (1H, d), 2.50 (3H, s), 2.7 (1H, dd), 2.90 (1H, m) 3.15 (3H, s), 3.28 (3H, s), 3.3 (1H, d), 3.35 (3H, s), 3.50 (1H, m), 3.65 (2H, d), 3.77 (1H, d,), 4.02 (3H, s), 4.30 (1H, t), 4.82 (1H, dd), 5.15 (1H, q, J=7 Hz), 5.90 (1H, dd), 6.25 (1H, s), 6.47 (1H, dd), 6.60 (1H, d), 6.75 (1H, d), 6.85 (1H, d).

Esterification of Maytansinol (2) with N-methyl-N-(3-methyldithio-propanoyl)-L-alanine (6b)

A solution of N-methyl-N-(3-methyldithio-propanoyl)-L-alanine (6b) (5.0 g, 21.5 mmol) in dry methylene chloride (80 mL) was stirred under an argon atmosphere, and treated sequentially with solutions of DCC (4.58 g, 22.2 mmol) in methylene chloride (54 mL), 1M ZnCl$_2$ in ether (4.4 mmol), and maytansinol (2) (2.0 g, 3.5 mmol) in methylene chloride (80 mL). The reaction mixture was stirred at room temperature for four hours, and then filtered.

A Diazem™ cyano preparative HPLC column (250 mm×50 mm, 10 micron particle size) was equilibrated in a mixture of hexanes:2-propanol:ethyl acetate (17:2:6, v/v/v) at a flow rate of 150 mL/min. A solution of the mixture of the L- and D-aminoacyl ester 10 of maytansinol (1 g in 25 mL ethyl acetate) was injected onto the column. Under these conditions, the desired L-isomer (10b) has a retention time of 42 min, while the D-isomer elutes at 56 min. Optically pure product is obtained by this method, and the recovery is >90%.

$^1$H NMR (CDCl$_3$) L-aminoacyl isomer (10b): δ0.84(3H, s), 1.11–1.23 (1H, m), 1.31 (3H, d, J=6 Hz), 1.35 (3H, d, J=7 Hz), 1.46–1.52 (1H, m), 1.68 (3H, s), 1.97 (1H, d, J=9 Hz), 2.24 (1H, dd, J=12 Hz and 15 Hz), 2.30 (3H, s), 2.65 (1H, dd, J=12 Hz and 15 Hz), 2.73–2.86 (2H, m), 2.90 (3H, s), 2.92–3.03 (2H, m), 3.08 (1H, d, J=9 Hz), 3.14 (1H, d, J=12 Hz), 3.28 (3H, s), 3.39 (3H, s), 3.54 (1H, d, J=9 Hz), 3.72 (1H, d, J=13 Hz), 4.02 (3H, s), 4.31 (1H, t, J=11 Hz), 4.82 (1H, dd, J=3 Hz and 12 Hz), 5.45 (1H, q, J=7 Hz), 5.69 (1H, dd, J=9 Hz and 15 Hz), 6.25 (1H, s), 6.47 (1H, dd, J=11 Hz and 15 Hz), 6.67 (1H, d, J=1.5 Hz), 6.77 (1H, d, J=11 Hz), 6.85 (1H, d, J=1.5 Hz).

Esterification of Maytansinol (2) with N-methyl-N-(methyldithiobutanoyl)-L-alanine (6c)

A solution of N-methyl-N-(methyldithiobutanoyl)-L-alanine (6c) (8.9 mg, 35.5 μmol) in dry methylene chloride (0.15 mL) was stirred under an atmosphere of argon, and treated sequentially with solutions of DCC (8.8 mg, 42.6 μmol) in methylene chloride, 1M ZnCl$_2$ (7.1 μmol) in ether and maytansinol (2) (4.0 mg, 7.1 μmol) in methylene chloride. The reaction mixture was stirred at room temperature for three hours, and then filtered and the filtrate was evaporated under reduced pressure, yielding a mixture of L- and D-aminoacyl esters of maytansinol. This material can be further purified using a Diazem™ cyano preparative HPLC column (250 mm×50 mm, 10 micron particle size) equilibrated in a mixture of hexanes:2-propanol:ethyl acetate (17:2:6, v/v/v) at a flow rate of 150 mL/min as described above for 10*b*.

Esterification of Maytansinol (2) with N-methyl-N-(phenyldithio-propanoyl)-L-alanine (6*e*)

A solution of N-methyl-N-(phenyldithio-propanoyl)-L-alanine (6*e*) (31.5 mg, 105 μmol) in methylene chloride (0.4 mL) was stirred under argon and treated sequentially with solutions of DCC (26 mg, 126 μmol) in methylene chloride, 1M $ZnCl_2$ (17.7 μmol) in ether and maytansinol (2) (10 mg, 17.7 μmol) in methylene chloride (0.2 mL). The reaction mixture was stirred at room temperature for three hours. The precipitate was removed by filtration and the filtrate concentrated under reduced pressure.

The mixture can be further purified using a Diazem™ cyano preparative HPLC column (250 mm×50 mm, 10 micron particle size) was equilibrated in a mixture of hexanes:2-propanol:ethyl acetate (17:2:6, v/v/v) at a flow rate of 150 mL/min as described above for (10*b*).

$^1$H NMR ($CDCl_3$) L-aminoacyl isomer (10*e*): δ0.82 (3H, s), 1.11–1.25 (1H, m), 1.33 (3H, d, J=3 Hz), 1.61 (3H, s), 1.63 (3H, d, J=14 Hz), 2.19 (1H, dd, J=13 Hz and 15 Hz), 2.61 (1H, dd, J=12 Hz and 15 Hz), 2.78 (3H, s), 2.68–3.03 (2H, m), 3.07 (1H, d, J=9 Hz), 3.20 (3H, s), 3.38 (3H, s), 3.53 (1H, d, J=9 Hz), 3.63 (1H, d, J=13 Hz), 3.68 (3H, s), 4.01 (3H, s), 4.30 (1H, t, J=11Hz), 4.79 (1H, dd, J=3 Hz and 8 Hz), 5.43 (1H, q, J=7 Hz), 5.68 (1H, dd, J=9 Hz and 15 Hz), 6.23 (1H, s), 6.45 (1H, dd, J=12 Hz and 15 Hz), 6.60 (1H, d, J=1.5 Hz), 6.75 (1H, d, J=12 Hz), 6.77 (1H, d, J=1.5 Hz), 7.22–7.40 (5H, m).

Esterification of Maytansinol (2) with N-methyl-N-(3-methyldithio-butanoyl)-L-alanine (6*g*)

A solution of N-methyl-N-(3-methyldithiobutanoyl)-L-alanine (6*g*) (23.2 mg, 0.088 mmol) in dichloromethane (0.2 mL) was stirred under an argon atmosphere, and treated sequentially with a solution of maytansinol (5 mg, 0.0088 mmol) in dichloromethane (0.2 mL), DCC (20.6 mg) in dichloromethane (0.2 mL) and 1M zinc chloride (0.0088 mmol) in ether. The reaction was stirred overnight at room temperature. The reaction mixture was then filtered and the solvent was evaporated. The residue was purified by preparative TLC on silica gel, using 6% methanol in chloroform to give the desired L-maytansinoid ester 10*g*. The product 10*g* can be more efficiently purified using a Diazem™ cyano preparative HPLC column (250 mm×10 mm, 10 micron particle size) equilibrated in a mixture of hexanes:2-propanol:ethyl acetate (17:2:6, v/v/v) at a flow rate of 4.70 mL/min as described above for (10*b*).

Esterification of Maytansinol (2) with N-acetyl-N-methyl methyldithiocysteine (9*a*)

A solution of N-Acetyl-N-methyl-methyldithiocysteine (9*a*) (15.6 mg, 0.07 mmol) in dry methylene chloride (0.45 mL) was stirred at room temperature under an argon atmosphere and treated sequentially with solutions of 1M $ZnCl_2$ in ethyl ether (0.028 mmol), DCC (17.3 mg, 0.084 mmol) in methylene chloride (0.2 mL), and maytansinol (2) (4.0 mg, 0.007 mmol) in methylene chloride (0.1 mL). The reaction mixture was stirred for three hours and then filtered and the filtrate evaporated under reduced pressure.

The residue can be further purified using a Diazem cyano preparative HPLC column (250 mm×50 mm, 10 micron particle size) was equilibrated in a mixture of hexanes:2-propanol:ethyl acetate (17:2:6, v/v/v) at a flow rate of 150 mL/min as described above for (10*b*).

Step 3
Reduction of Disulfide-Containing Maytansinoid

A solution of the disulfide-containing L-aminoacyl ester of maytansinol 10*b* (1.95 g, 2.5 mmol) in a mixture of ethyl acetate (140 mL) and methanol (210 mL) was stirred at room temperature under an argon atmosphere, and treated with a solution of dithiothreitol (0.95 g, 6.2 mmol) in 0.05 M potassium phosphate buffer (140 mL), pH 7.5, containing 2 mM ethylenediaminetetraacetic acid (EDTA). The progress of the reaction was monitored by HPLC and was complete in three hours.

The completed reaction mixture was treated with a solution of 0.2 M potassium phosphate buffer (250 mL), pH 6.0, containing 2 mM EDTA, and then extracted with ethyl acetate (3×600 mL). The organic layers were combined, washed with brine (100 mL) and then dried over sodium sulfate. Evaporation of the solvent gave a residue of crude thiol-containing maytansinoid 11*b*.

The crude thiol-containing maytansinoid 11*b* was purified by HPLC using a preparative Diazem™ cyano HPLC column (250 mm×50 mm, 10 micron particle size) that was equilibrated in a mixture of hexanes:2-propanol:ethyl acetate (78.0:5.5:16.5, v/v/v) and ran at a flow rate of 150 mL/min. Thiol-containing maytansinoid 11*b* eluted as peak centered at 16 min. Fractions containing the product were evaporated to give pure thiol-containing maytansinoid 11*b* as a white solid (76% yield with a purity of 99%).

The presence of one mole of sulfhydryl group/mol product was confirmed using Ellman's assay. The product was further characterized by NMR spectroscopy. $^1$H NMR ($CDCl_3$): δ0.84 (3H, s), 1.33 (3H, d, J=5 Hz), 1.35 (3H, d, J=5 Hz), 1.60 (3H, s), 1.68 (3H, s), 2.22 (1H, dd, J=3 Hz and 14 Hz, 2.60–2.82 (2H, m), 2.88 (3H, s), 3.08–3.20 (2H, m), 3.25 (3H, s), 3.39 (3H, s), 3.55 (1H, d, J=9 Hz), 3.71 (1H, d, J=12 Hz), 4.02 (3H, s), 4.32 (1H, t, J=10 Hz), 4.81 (1H, dd, J=3 Hz and 12 Hz), 5.45 (1H, q, J=7 Hz), 5.67 (1H, dd J=9 Hz and 15 Hz), 6.25 (1H, s), 6.47 (1H, dd, J=11 Hz and 15 Hz), 6.70 (1H, d, J=1.5 Hz), 6.75 (1H, d, J=11 Hz), 6.86 (1H, d, J=1.5 Hz).

While the invention has been described in detail and with reference to specific embodiments thereof, it will be apparent to one skilled in the art that various changes and modifications can be made therein without departing from the spirit and scope thereof.

What is claimed is:

1. A process for preparing a thiol-containing maytansinoid wherein the thiol group is part of the ester moiety at C-3, comprising the steps of:

(1) conducting reductive hydrolysis of a maytansinoid C-3 ester with a reducing agent selected from the group consisting of lithium trimethoxyaluminum hydride (LiAl(OMe)$_3$H), lithium triethoxyaluminum hydride (LiAl(OEt)$_3$H) and lithium tripropoxyaluminum hydride (LiAl(OPr)$_3$H), to yield a maytansinol;

(2) purifying the maytansinol to remove side products when present;

(3) esterifying the purified maytansinol with a carboxylic acid to yield a reaction mixture of an L- and a D-aminoacyl ester of maytansinol;

(4) separating the L-aminoacyl ester of maytansinol from the reaction mixture in (3);

(5) reducing the L-aminoacyl ester of maytansinol to yield a thiol-containing maytansinoid; and (6) purifying the thiol-containing maytansinoid.

2. The process of claim 1, wherein the reducing agent in (1) is lithium trimethoxyaluminum hydride.

3. The process of claim 1, wherein the reducing agent in (1) is used in a concentration of from about 5 to 100 equivalents per mole of the maytansinoid C-3 ester.

4. The process of claim 1, wherein the reducing agent in (1) is used in a concentration of from about 7.5 to 30 equivalents per mole of the maytansinoid C-3 ester.

5. The process of claim 1, wherein the reducing agent in (1) is used in a concentration of from about 10 to 20 equivalents per mole of the maytansinoid C-3 ester.

6. The process of claim 1, wherein the reductive hydrolysis in (1) is conducted at a temperature of from about −80° C. to 0° C.

7. The process of claim 1, wherein the reductive hydrolysis in (1) is conducted at a temperature of from about −45° C. to −27.5° C.

8. The process of claim 1, wherein the reductive hydrolysis in (1) is conducted at a temperature of from about −35° C. to −30° C.

9. The process of claim 1, wherein the reducing agent in (1) is added over a period of from about 5 to 40 minutes.

10. The process of claim 1, wherein the reducing agent in (1) is added over a period of from about 7 to 20 minutes.

11. The process of claim 1, wherein the reducing agent in (1) is added over a period of from about 8 to 12 minutes.

12. The process of claim 1, wherein the maytansinol is purified in (2) by chromatography.

13. The process of claim 12, wherein the chromatography is silica gel column chromatography, preparative thin-layer chromatography on silica gel or cyano-bonded silica HPLC column chromatography.

14. The process of claim 12, wherein the chromatography is silica gel column chromatography.

15. The process of claim 12, wherein the purification is performed at ambient temperature.

16. The process of claim 12, wherein the maytansinol is purified to a purity of about 95%.

17. The process of claim 1, wherein the carboxylic acid in (3) is selected from the group consisting of N-methyl-N-methyldithioacetyl-L-alanine, N-methyl-N-(3-methyldithio-propanoyl)-L-alanine, N-methyl-N-(3-methyldithio-butanoyl)-L-alanine, N-methyl-N-(4-methyldithio-butanoyl)-L-alanine, N-methyl-N-(5-methyldithio-pentanoyl)-L-alanine, N-methyl-N-(3-phenyldithio-propanoyl)-L-alanine, N-methyl-N-(3-(4-nitrophenyldithio)propanoyl)L-alanine, N-acetyl-N-methyl-methyldithiocysteine and N-acetyl-N-methyl-methyldithiohomocysteine.

18. The process of claim 1, wherein the carboxylic acid in (3) is N-methyl-N-(3-methyldithio-propanoyl)-L-alanine.

19. The process of claim 1, wherein the esterification in (3) is conducted at ambient temperature.

20. The process of claim 1, wherein the esterification in (3) further comprises the use of dicyclohexylcarbodiimide and zinc chloride.

21. The process of claim 1, wherein the separating in (4) is carried out by passing the reaction mixture over a cyano-bonded silica HPLC column.

22. The process of claim 1, wherein the separating in (4) is carried out at about 25° C.

23. The process of claim 1, wherein the reduction in (5) uses dithiothreitol as the reducing agent.

24. The process of claim 1, wherein the reduction in (5) is carried out in a mixture of ethyl acetate-methanol-aqueous buffer which is capable of keeping buffer salts, dithiothreitol, unreduced maytansinoids and reduced maytansinoids in solution.

25. The process of claim 24, wherein the mixture of ethyl acetate-methanol-aqueous buffer is 1:1.5:1, v/v/v, ethyl acetate:methanol:aqueous buffer.

26. The process of claim 24, wherein the concentration of the thiol-containing maytansinoid is such that the thiol-containing maytansinoid remains soluble in ethyl acetate-methanol-aqueous buffer.

27. The process of claim 26, wherein the concentration of the thiol-containing maytansinoid is about 4 g/L.

28. The process of claim 1, wherein the reduction in (5) is carried out in an oxygen-free atmosphere.

29. The process of claim 1, wherein the reduction in (5) is carried out at about 25° C.

30. The process of claim 1, wherein the purifying of the thiol-containing maytansinoid in (6) is by chromatography.

31. The process of claim 30, wherein the purifying of the thiol-containing maytansinoid in (6) is by a cyano-bonded HPLC column chromatography.

32. The process of claim 31, wherein the chromatography is by a cyano-bonded HPLC column equilibrated and run in an organic solvent.

33. The process of claim 32, wherein the organic solvent is a mixture of hexanes:2-propanol:ethyl acetate.

34. The process of claim 33, wherein the organic solvent is a 78.0:5.5:16.5, v/v/v, mixture of hexanes:2-propanol:ethyl acetate.

* * * * *